US009616213B2

(12) United States Patent
Furnish et al.

(10) Patent No.: US 9,616,213 B2
(45) Date of Patent: Apr. 11, 2017

(54) MEDICAL VALVE WITH A VARIABLE DIAMETER SEAL

(71) Applicant: Freudenberg Medical, LLC, Carpinteria, CA (US)

(72) Inventors: Greg Furnish, Louisville, KY (US); Anthony Appling, Crestwood, KY (US); Ben Morris, Jeffersonville, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 239 days.

(21) Appl. No.: 14/326,593

(22) Filed: Jul. 9, 2014

(65) Prior Publication Data
US 2016/0008591 A1   Jan. 14, 2016

(51) Int. Cl.
*A61M 5/14* (2006.01)
*A61M 39/06* (2006.01)
*A61B 1/00* (2006.01)
*A61B 1/018* (2006.01)

(52) U.S. Cl.
CPC ..... *A61M 39/0613* (2013.01); *A61B 1/00137* (2013.01); *A61B 1/018* (2013.01); *A61M 39/06* (2013.01); *A61M 2039/062* (2013.01); *A61M 2039/0633* (2013.01); *A61M 2039/0673* (2013.01)

(58) Field of Classification Search
CPC .............. A61B 17/3462; A61M 39/06; A61M 39/0613; A61M 2039/0673; A61M 2039/062; A61M 2039/0633
USPC ............................................. 604/167.03, 256
See application file for complete search history.

(56) References Cited

U.S. PATENT DOCUMENTS

| 5,484,418 | A  | 1/1996  | Quiachon et al. |
| 5,634,908 | A  | 6/1997  | Loomas |
| 6,458,103 | B1 | 10/2002 | Albert et al. |
| 6,572,590 | B1 | 6/2003  | Stevens et al. |
| 7,967,790 | B2 | 6/2011  | Whiting et al. |
| 8,025,641 | B2 | 9/2011  | Bettuchi |

(Continued)

FOREIGN PATENT DOCUMENTS

| EP | 0426407 A2    | 5/1991  |
| JP | 200316986 A   | 11/2000 |
| WO | 2005058409 A1 | 6/2005  |

OTHER PUBLICATIONS

Search Report issued Nov. 23, 2015 in corresponding European Patent Application No. 15175941.2.

*Primary Examiner* — Edelmira Bosques
(74) *Attorney, Agent, or Firm* — Dickinson Wright, PLLC (57) ABSTRACT

A medical valve assembly includes a tube extending between a first tube end and a second tube end to define a passageway extending along a longitudinal axis between the ends. A plunger plate extends radially from the second tube end of the tube, and a valve housing surrounds the tube about the second tube end and extends from a first valve housing end to a second valve housing end. The valve housing includes a flange extending radially inwardly from the second valve housing end and disposed in spaced relationship with the plunger plate to define a distance dimension D extending therebetween. An elastomeric seal is compressed between the plunger plate and the flange, and one of the valve housing and the tube is axially movable relative to the other to vary the distance between said plunger plate and said flange and adjust an inner diameter of the elastomeric seal.

12 Claims, 7 Drawing Sheets

(56) References Cited

U.S. PATENT DOCUMENTS

2004/0178586 A1 9/2004 Junge
2011/0264105 A1 10/2011 Barthold
2012/0238958 A1 9/2012 Moore
2012/0310166 A1 12/2012 Huff

MEDICAL VALVE WITH A VARIABLE DIAMETER SEAL

BACKGROUND OF THE INVENTION

1. Field of the Invention

The present disclosure relates generally to medical devices and procedures. In particular, the present disclosure relates to hemostatic valves and systems, and methods of using the same.

2. Description of the Prior Art

This section provides background information related to the present disclosure which is not necessarily prior art.

Numerous procedures have been developed that involve the percutaneous insertion of a medical device into a body vessel of a patient, with the medical device being introduced into the vessel by a variety of known techniques. Each of these procedures must control the flow of bodily fluids when the medical device is inserted into the body vessel. Accordingly, medical valves, such as hemostatic valves, iris valves, laproscopic ports, or the like, are often used to limit or prevent blood loss during the procedure.

Hemostatic valves often incorporate a disk valve to control fluid flow through the medical device. However, disk valves are subject to deformation with both time and use, and often can tear or become dislodged during insertion and/or withdrawal of the medical device. Furthermore, disk valves are not designed to provide an effective seal across a wide range of differently sized medical devices. Although the disk valve can be modified to accommodate these situations, such as with increased tensile and/or elongation properties, this modification leads to increased resistance, and thus require the use of excessive force, when the medical device is inserted and withdrawn through the disk valve.

Iris valves can include an elastomeric sleeve that is disposed within a valve body and which is interconnected to a rotatable cap. When the cap is rotated in a first direction, an opening extending through the elastomeric sleeve is opened. Conversely, when the cap is rotated in a second opposite direction, the elastomeric sleeve is twisted and constricted to effectuate a closure of the elastomeric sleeve. However, if the operator stops the rotation, the elastomeric sleeve can revert, or recoil, back to the open position. Additionally, even when the elastomeric sleeve is held in the closed position, gaps or channels extend therethrough as a result of the twisting or infolding required to effectuate a closure. Accordingly, fluid can leak through the iris valve in the closed position. Further, the continuous twisting and constricting of the elastomeric sleeve leads to wear of the sleeve, such as through tearing.

The drawbacks associated with the existing medical valves are further exemplified when one considers that a single medical valve often is used to insert multiple medical devices during a single procedure. For example, a hemostatic valve may be used first for introducing a delivery catheter, followed by an interventional catheter. In this example, the hemostatic valve must be able to provide a hemostatic seal under a variety of conditions, i.e., accommodate a variety of different sized medical devices. Additionally, the hemostatic valve device must be able to quickly adjust to use of each of these different medical devices, otherwise significant fluid loss can occur through the medical valve.

SUMMARY OF THE INVENTION

This section provides a general summary of the disclosure and is not intended to be a comprehensive disclosure of its full scope, aspects, objectives, and/or all of its features.

A medical valve assembly for use in inserting a medical device into a body vessel of a patient includes a tube extending between a first tube end and a second tube end to define a passageway extending longitudinally along an axis between the ends. A plunger plate extends radially from the second tube end and a valve housing surrounds the tube about the second tube end. The valve housing extends from a first valve housing end to a second valve housing end and includes a flange extending radially inwardly from the second valve housing end, with the flange disposed in spaced relationship with respect to the plunger plate so as to define a distance dimension therebetween. An elastomeric seal is compressed between the plunger plate and the flange and has an inner diameter for use in establishing a variable seal of the medical valve assembly. One of the valve housing and the tube is axially movable relative to the other to vary the distance between the plunger plate and the flange and adjust the inner diameter of the elastomeric seal for variably sealing the medical valve assembly to a variety of differently sized medical devices. A manual actuator is provided to controllably vary the distance dimension between the valve housing and the tube for proportionately varying a compression load applied to the elastomeric seal. In other words, axial movement of one of the valve housing or the tube relative to the other varies the compression load and allows the inner diameter of the elastomeric seal to be varied or adjusted in size. As a result, the size of the inner diameter of the elastomeric seal is able to be quickly and easily adjusted by a user to allow the medical valve assembly to be used with a variety of differently sized medical devices, even during the same procedure.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to medical valve assemblies of the type used to introduce and withdrawal a medical device (i.e., a guide wire, catheter, stent, filter, etc.) into a body vessel of a patient. In particular, each of the medical valve assemblies of the present disclosure incorporate a variable seal arrangement and a manually-operable actuator for controlling an entry dimension of the variable seal arrangement.

Figure 1:
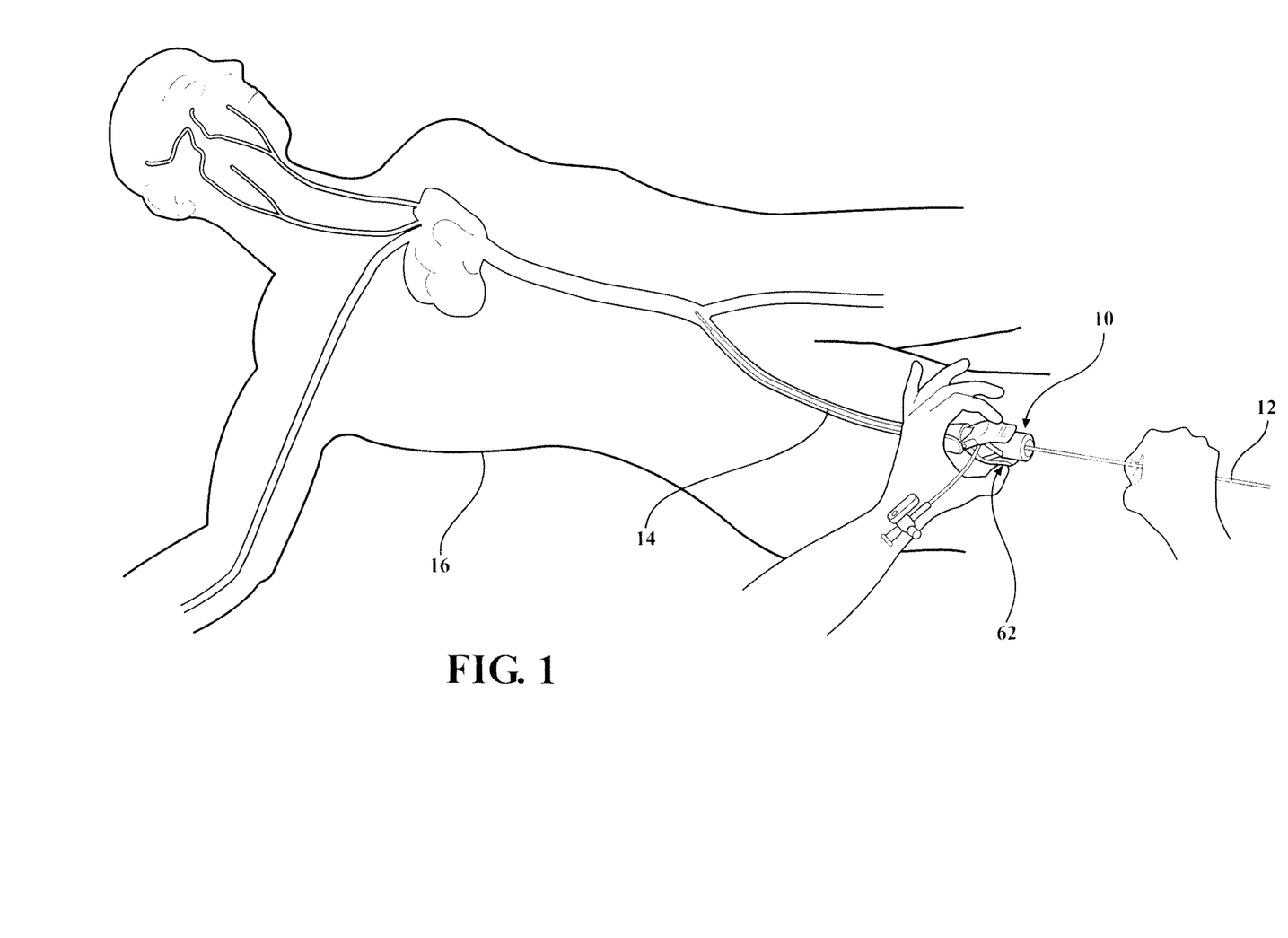
FIG. 1 is an environmental view of a first embodiment of a medical valve constructed in accordance with the principles of the present disclosure and illustrating a user interacting therewith.
Figure 2:
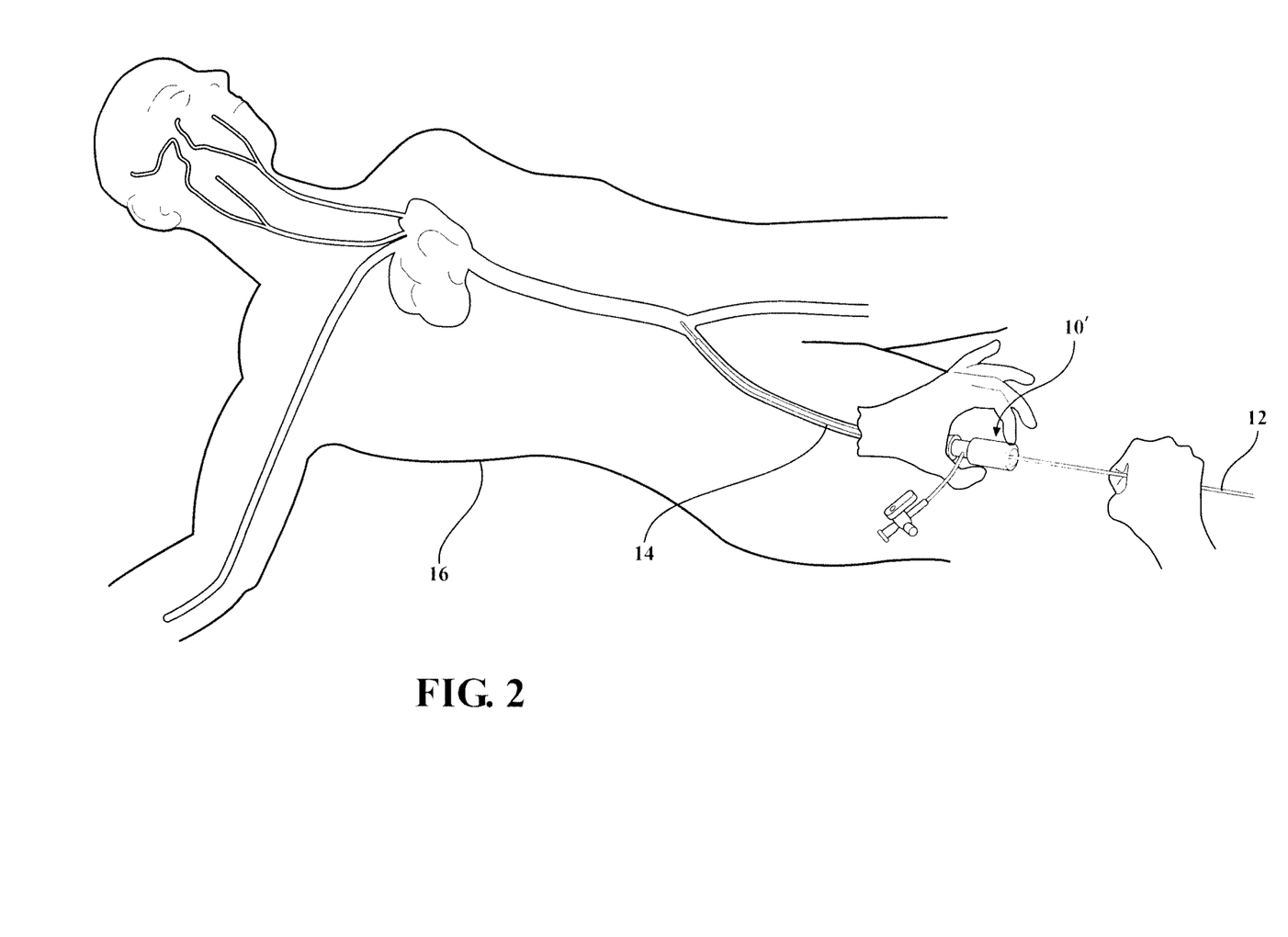
FIG. 2 is an environmental view of a second embodiment of the medical valve constructed in accordance with the principles of the present disclosure and illustrating the user interacting therewith.

Referring to the Figures, wherein like numerals indicate corresponding parts throughout the several views, an environmental view of a first embodiment of a medical valve assembly 10 and a second embodiment of a medical valve assembly 10' is generally shown in FIGS. 1 and 2, respectively. As illustrated therein, each medical valve assembly 10, 10' is of the type for use with a medical device 12, such as a guide wire, catheter, stent, filter, vessel occlusion device, or the like. As will be explained in more detail below, as the medical device 12 is inserted and guided through the medical valve assembly and into a body vessel 14 of a patient 16, a user can manually actuate or interact with the medical valve assembly to effectuate a variable seal with variety of different sized medical devices 12.

Figure 4A:
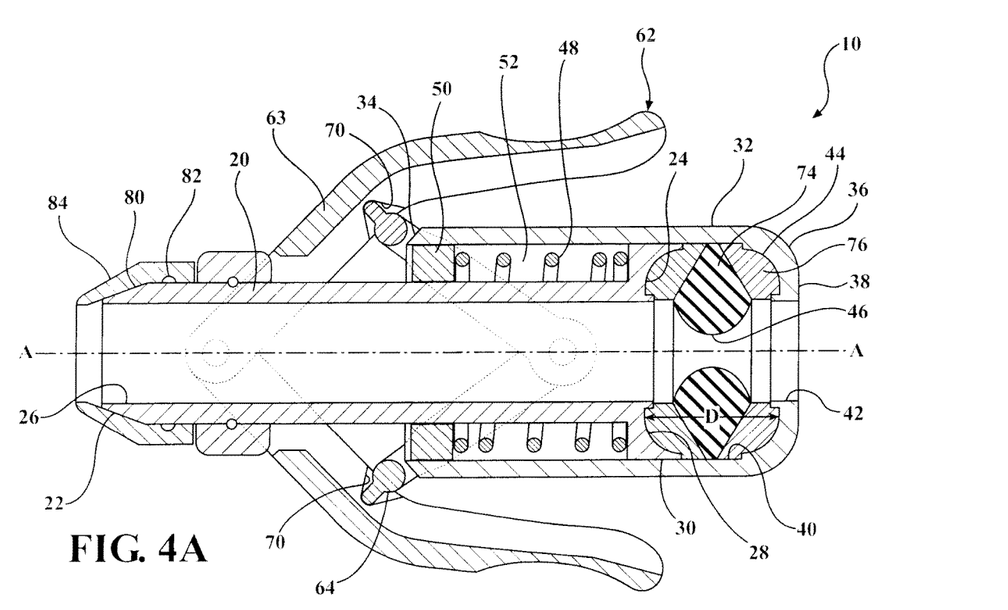
FIG. 4A is a cross-sectional view of the first embodiment of the medical valve illustrating a closed condition.
Figure 4B:
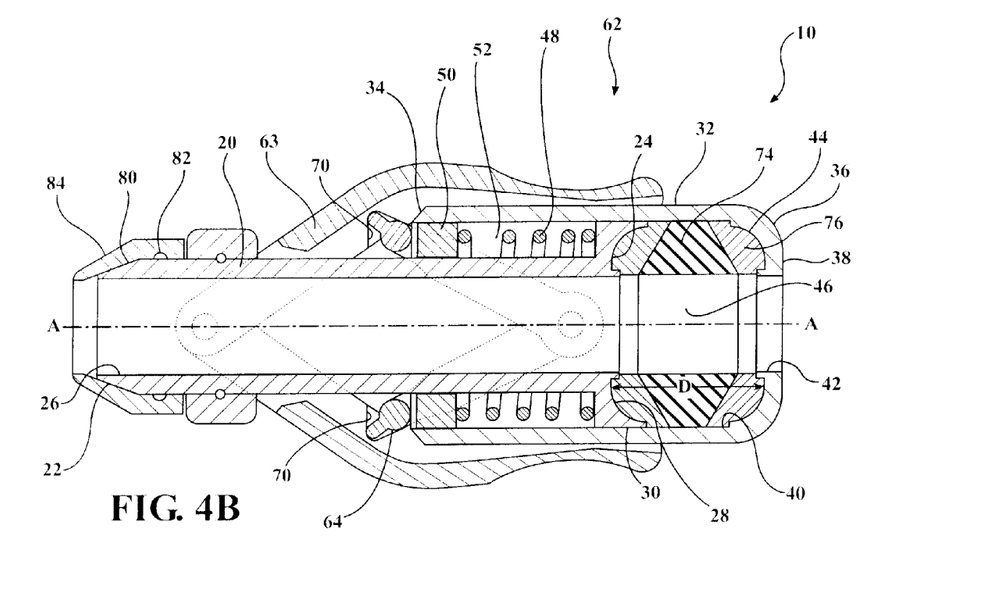
FIG. 4B is a cross-sectional view of the first embodiment of the medical valve illustrating an open condition.
Figure 9:
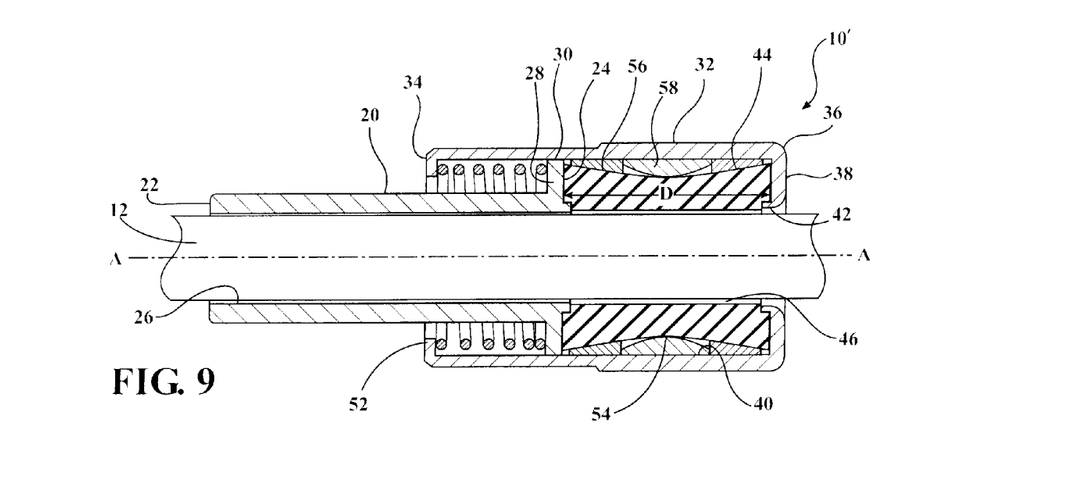
FIG. 9 is a cross-sectional view of the second embodiment shown in FIG. 8.

As best shown in FIGS. 4A, 4B and 9, the medical valve assemblies 10, 10' each include a tube 20 extending between a first tube end 22 and a second tube end 24 to define a passageway 26 extending longitudinally along an axis A between the ends 22, 24, with the passageway 26 being sized to receive a variety of differently sized medical devices 12. In this instance, the first tube end 22 is a distal tube end and the second tube end is a proximal tube end 24. A plunger plate 28 extends radially from the second tube end 24 to define an outer plunger plate surface 30 extending in spaced and parallel relationship to the axis A. A valve housing 32 is disposed in surrounding relationship with the tube 20 about the second tube end 24 and extends from a first valve housing end 34 to a second valve housing end 36 to overlay the outer plunger plate surface 30. In this instance, the first valve housing end 34 is a distal valve housing end and the second valve housing end 36 is a proximal valve housing end 36. As best shown in FIGS. 4A, 4B and 9, the valve housing 32 is disposed in spaced and parallel relationship with the tube 20 between the first valve housing end 34 and the plunger plate 28.

The valve housing 32 includes a flange 38 extending radially inwardly from the second valve housing end 36. The flange 38 is disposed in spaced relationship with the plunger plate 28 to define a distance dimension D, as well as a cavity 40, extending therebetween. The flange 38 also defines an opening 42 aligned on the axis A and that is sized to receive a variety of differently sized medical devices 12. An elastomeric seal 44 is installed in the cavity 40 and normally is pre-loaded or compressed between the plunger plate 28 and the flange 38. The elastomeric seal 44 is used to establish a variable seal of the medical valve assembly 10, 10'. In both of the first and second embodiments of the medical valve assembly 10, 10', one of the valve housing 32 or the tube 20 is axially movable relative to the other to vary the distance dimension D between the plunger plate 28 and the flange 38 for effectuating an adjustment of an inner diameter 46 of the elastomeric seal 44. In other words, the axial movement of one of the valve housing 32 or the tube 20 relative to the other results in a change in the compression load exerted on the elastomeric seal 44 which, in turn, allows the inner diameter 46 of the elastomeric seal 44 to be varied or adjusted in size. As best shown in FIGS. 4A, 4B and 9, when the valve housing 32 or the tube 20 is axially moved, the plunger plate 28 or the valve housing 32 axially slides relative to the other along the outer plunger plate surface 30. In other words, the outer plunger plate surface 30 guides a sliding axial movement between the valve housing 32 and the tube 20.

As best shown in FIGS. 4A, 4B, and 9, a compression member 48, 54 is disposed within the valve housing 32 and is compressed against the plunger plate 28 for normally closing or decreasing the inner diameter 46 to establish a closed position of the elastomeric seal 44. As a result, the compression member 48, 54 is arranged to effectuate a closing or decreasing of the inner diameter 46 of the elastomeric seal 44 to establish a closed condition of the medical valve assembly 10, 10'. In its closed condition, the elastomeric seal 44 completely isolates or seals the opening 42 of the valve housing 32 from the passageway 26 of the tube 20. The valve housing 32 or the tube 20 is then axially movable relative to the other to alter a distance D between the flange 38 and the plunger plate 28 and shift the medical valve assembly 10, 10' from the closed condition to an open/operative condition. The altered or varied distance D between the flange 38 and the plunger plate 28 allows the elastomeric seal 44 to expand, and as a result, the inner diameter 46 of the elastomeric seal 44 is expanded or increased to move the elastomeric seal 44 from its closed position to an open position. With the elastomeric seal 44 in its open position, the medical device 12 is positioned to be inserted serially through the opening 42, the inner diameter 46 of the elastomeric seal 44 and the passageway 26 of the medical valve assembly 10.

As best shown in FIGS. 4A and 4B, in the first embodiment of medical valve assembly 10, the compression member 48, 54 comprises a coil spring 48 radially disposed between the valve housing 32 and the tube 20 and compressed between the first valve housing end 34 and the plunger plate 28. However, any other suitable compression member could be utilized without departing from the scope of the subject disclosure. In a preferred embodiment, a disk 50 is slidably disposed around the tube 20 and interconnected to the first valve housing end 34 to establish a shoulder 52 extending radially inward from the valve housing 32 and which is disposed in engagement with the coil spring 48. The coil spring 48 acts to bias the valve housing 32 towards the first tube end 22 for compressing the elastomeric seal 44 between the flange 38 and the plunger plate 28 and normally position the elastomeric seal 44 in its closed position. The valve housing 32 is then axially movable from the closed position and relative to the tube 20 to increase the distance D between the flange 38 and the plunger plate 28. The increased distance D allows the elastomeric seal 44 to expand in an increased area of the cavity 40 disposed between the flange 38 and the plunger plate 28, and as a result, the inner diameter 46 of the elastomeric seal 44 is expanded or increased, thereby opening the elastomeric seal 44. The result is the establishment of the open condition of the medical valve assembly 10.

Figure 8:
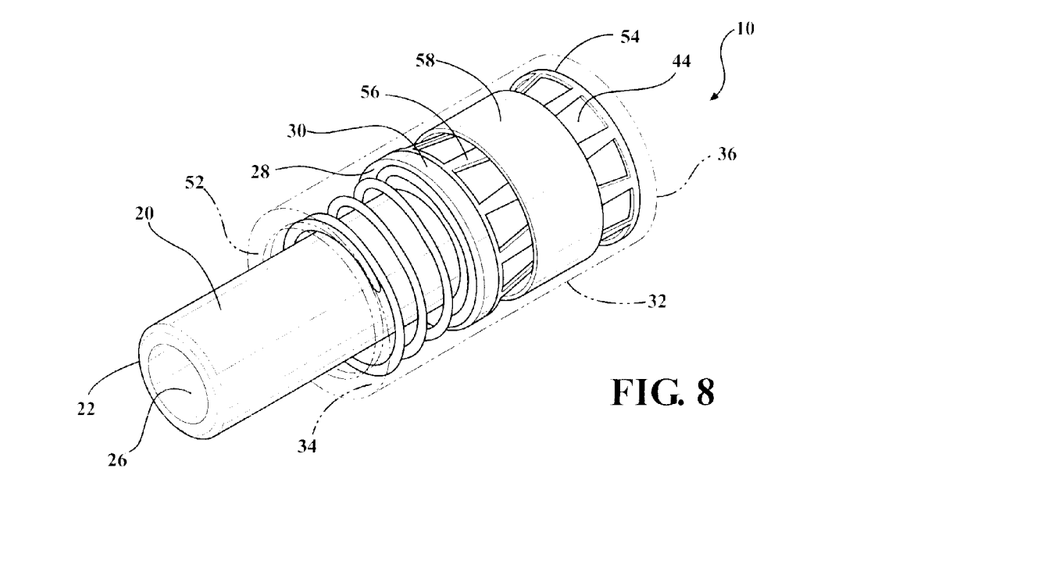
FIG. 8 is a perspective view of the second embodiment of a medical valve constructed in accordance with the present disclosure.

As best shown in FIGS. 8 and 9, in the second embodiment of the medical valve assembly 10', the compression member 48, 54 also comprises a coil spring 48 radially disposed between the valve housing 32 and the tube 20 and compressed between the first valve housing end 34 and the plunger plate 28. However, any other suitable compression member could be utilized without departing from the scope of the subject disclosure. The valve housing 32 defines a shoulder 52 extending radially inward from the first valve housing end 34 and slidably disposed around the tube 20. The shoulder 52 is disposed in engagement with the coil spring 48, and the coil spring 48 acts to bias the valve housing 36 towards the first tube end 22. In a preferred embodiment, the compression member 48, 54 additionally includes a leaf spring cage 54 disposed in surrounding relationship with the elastomeric seal 44. However, any other suitable compression member could be utilized without departing from the scope of the subject disclosure. The leaf spring cage 54 extends between the plunger plate 28 and the flange 38 and is compressed therebetween by way of the compression spring 48. The leaf spring cage 54 includes a plurality of struts 56 each extending axially along the leaf spring cage 54 and configured to fold radially inward towards the elastomeric seal 44 when the valve housing 36 is axially biased towards the first tube end 22 by the compression spring 48. As a result, the distance D between the plunger plate 28 and the flange 38 is decreased, thus causing the elastomeric seal 44 to compress and reduce the inner diameter 46. Put another way, the coil spring 48 and the leaf spring cage 54 interact to compress the elastomeric seal 44 between the flange 38 and the plunger plate 28 and normally position the elastomeric seal 44 in its closed position. As a medical device 12 is inserted through the passageway 26, the medical device 12 engages the elastomeric seal 44 with an insertion force that is transferred or exerted radially outward on the struts 56 of the leaf spring cage 54, causing the leaf spring cage 54 to expand and counteract the biasing force of the coil spring 48. As a result, the distance between the plunger plate 28 and the flange 38 is increased, allowing the inner diameter 46 of the elastomeric seal 44 to expand or increase and establish the open condition of the medical valve assembly 10'. A constrictor band 58 extends around the leaf spring cage 54 to prevent the plurality of struts 56 from engaging the valve housing 32 when the leaf spring cage 54 is expanded by the insertion force of the medical device 12.

Figure 3:
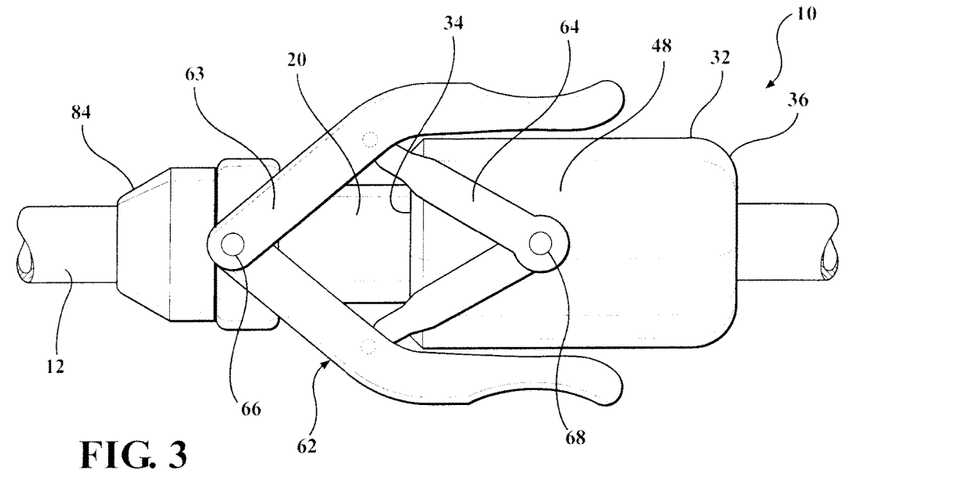
FIG. 3 is a perspective view of the first embodiment of the medical valve illustrating a scissor-type manual actuator.
Figure 6:
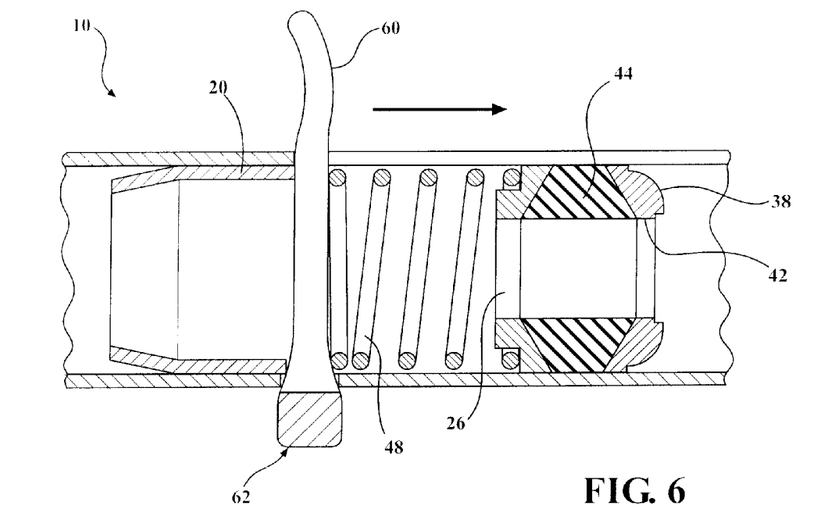
FIG. 6 is a cross-sectional view of the first embodiment of the medical valve illustrating an alternative arrangement for the manual actuator.

As best shown in FIGS. 3, 4A, and 4B, the first embodiment of the medical valve assembly 10 includes a manual actuator 62 which can be connected to the valve housing 32 for allowing a user to interact with the medical valve assembly 10 and vary a size of the inner diameter 46 of the elastomeric seal 44. Put another way, the user can interact with the manual actuator 62 to overcome the bias of the compression member 48 and move the valve housing 32 relative to the tube 20 along the axis A towards the second tube end 24. As a result, the manual actuator 62 allows the user to manually establish the open condition of the medical valve assembly 10. As best shown in FIG. 6, in the alternative embodiment, the manual actuator 62 can include a trigger arm 60 extending radially from the valve housing 32. In this situation, the user can pull back on the trigger arm 60 to establish the open condition of the medical valve assembly 10. In other words, a user can pull back the trigger arm 60 to vary the bias on the plunger plate 28.

Figure 7:
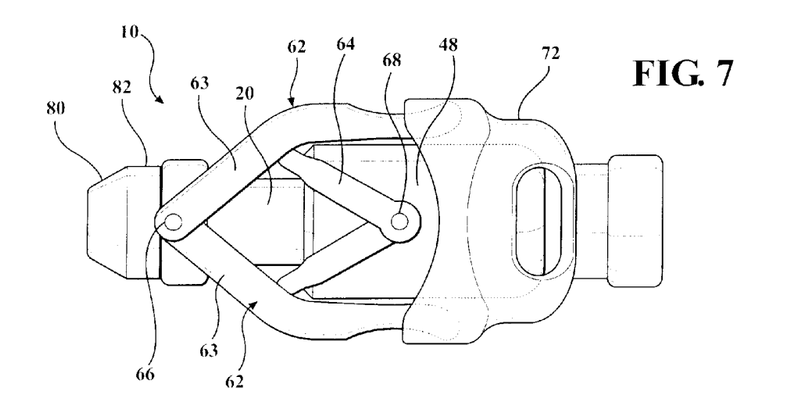
FIG. 7 is a perspective view of the first embodiment illustrating a detachable cap disposed over a pair of lever arms associated with the scissor-type manual actuator.

As best shown in FIGS. 3 and 4, the manual actuator 62 can include a pair of lever arms 63 interconnected between the tube 20 and the valve housing 32 by way of a pair of lever linkages 64. As best shown in FIG. 3, each lever arm 63 includes a first pivot 66 extending radially from the tube 20 and each lever linkage 64 includes a second pivot 68 extending radially from the valve housing 32. The pair of lever arms 63 are pivotably connected to the tube 20 by the first pivots 66 and the pair of lever linkages 64 are pivotably connected to the valve housing by the second pivots 68 with each of the lever linkages 64 extending from the respective second pivot 68 to engage one of the respective lever arms 63. As best shown in FIG. 7, in a preferred embodiment, each of the lever arms 63 can also define a track 70 for receipt of the respective lever linkage 64 when the lever linkages 64 are disposed in abutting relationship with the lever arms 63. This arrangement of the lever arms 63 and the lever linkages 64 allows the user to squeeze or compress the pair of lever arms 63 with a specific force to axially advance the valve housing 32 by way of the lever linkages 64. As a result, the transferred force effectuates the increase in the distance D between the plunger plate 28 and the flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

Figure 10:
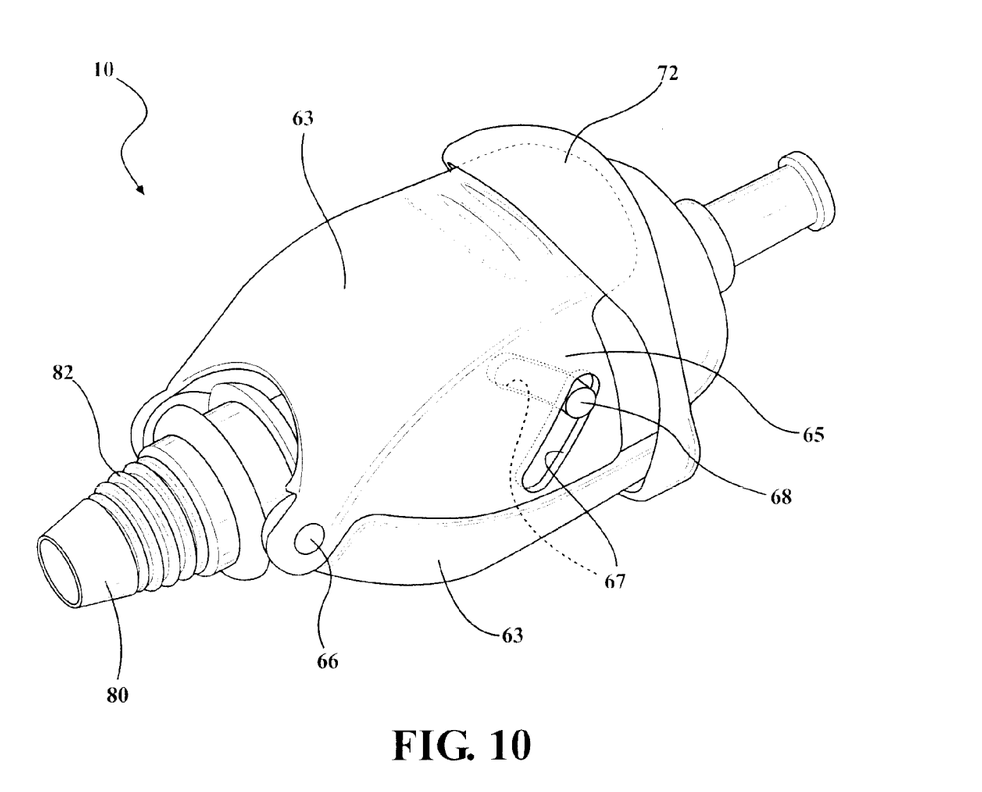
FIG. 10 is a perspective view of the first embodiment illustrating an alternative arrangement of the scissor-type manual actuator.

As best shown in FIG. 10, in an alternative arrangement the pair of lever arms 63 can be interconnected between the tube 20 and the valve housing 32 by way of a pair of plates 65. In a preferred embodiment, each lever arm 63 includes a plate 65 which extends radially therefrom and which defines a cam slot 67 for receiving the second pivot 68 extending radially from the valve housing 32. This arrangement of the lever arms 63 and the plates 65 allows the user to squeeze or compress the pair of lever arms 63 with a specific force to slide the second pivot 68 along the cam slots 67 and axially advance the valve housing 32 by way of the plates 65. As a result, the transferred force effectuates the increase in the distance D between the plunger plate 28 and the flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

As best shown in FIG. 7, a detachable cap 72 can be snapped or disposed over the second valve housing end 36 of the valve housing 32 to hold the pair of lever arms 63 in the radially compressed position when the medical valve assembly 10 is not in use. When the detachable cap 72 is in place, it keeps the elastomeric seal 44 in the open position, and thus increases the shelf life by reducing material creep, material sticking, and/or the distorting of the elastomeric seal 44.

Figure 5:
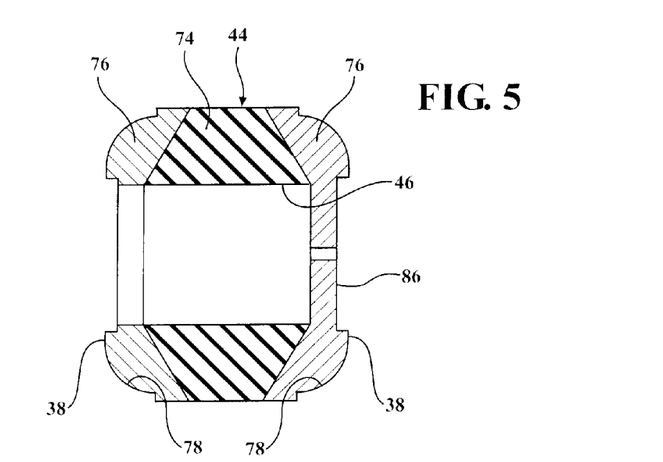
FIG. 5 is a partial view taken from FIG. 3 illustrating an elastomeric seal of the medical valve.

As best shown in FIG. 5, the elastomeric seal 44 can include an inner portion 74 and an outer portion 76 disposed axially outwardly from the inner portion 74. In a preferred embodiment, the inner portion 74 is made from a first material having a first durometer value and the outer portion 76 is made from a second material having a second durometer value being greater than the first durometer value. In other words, the elastomeric seal 44 includes an outside portion 76 that is harder than an inside portion 74. As further shown in FIGS. 4A and 4B, the outer portion 76 of the elastomeric seal 44 is disposed in compressed relationship with the plunger plate 28 and the flange 38. In a preferred embodiment, the plunger plate 28 and the flange 38 can include curved portions 78 to improve the retention and compression of the outer portions 76 of the elastomeric seal 44.

As best shown in FIG. 4, the tube 20 has a tapered portion 80 disposed adjacent the first tube end 22 for fitting a sheath over the tube 20. The tube 20 includes threads 82 disposed adjacent the first tube end 22 and a nose cap 84 is threadingly secured to the first tube end 22 for establishing a compression fit of the sheath between the nose cap 84 and the tapered portion 80 of the tube 20. Although not expressly shown, a wiper seal can be disposed within the passageway 26 between the elastomeric seal 44 and the first tube end 22 to provide a level of hemostasis around a larger device while the elastomeric seal 44 is opened for insertion of the medical device 12. Alternatively, as best shown in FIG. 5, a wiper seal 86 can be incorporated into the elastomeric seal 44 and extends radially inward from one of the outside portions 76. As a result, when the elastomeric seal 44 is inserted in the cavity 40, the wiper seal 86 is disposed adjacent the opening 42 of the valve housing 32.

It will be appreciated by those skilled in the art that the medical valve assembly 10' shown in FIGS. 8 and 9 can be equipped with the compression type manual actuator 62 shown in FIGS. 3, 4 and 7 or, in the alternative, the pull-type manual actuator 60 shown in FIG. 6. Likewise, alternative configurations are contemplated for manual actuators that function to controllably vary the relative axial position between two components for proportionately controlling the compression load applied to an elastomeric seal to regulate an internal opening dimension defined thereby.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical valve assembly for use in inserting a medical device into a body vessel of a patient, comprising:
a tube extending between a first tube end and a second tube end to define a passageway extending along a longitudinal axis between said ends;
a plunger plate extending radially from said second tube end of said tube;
a valve housing surrounding said tube about said second tube end and extending from a first valve housing end to a second valve housing end;
said valve housing including a flange extending radially inwards from said second valve housing end and disposed in spaced relationship with said plunger plate to define a distance extending therebetween;
an elastomeric seal compressed between said plunger plate and said flange and having an inner diameter for use in establishing a variable seal of the medical valve assembly;
a compression member disposed within said valve housing and biased against said plunger plate for decreasing said inner diameter to establish a closed condition of the medical valve assembly;
a manual actuator connected to said valve housing for allowing a user to overcome the bias of said compression member and effectuate axial movement of said valve housing relative to said tube to vary the distance between said plunger plate and said flange and adjust said inner diameter of said elastomeric seal for variably sealing the medical valve assembly to a variety of differently sized medical devices;
wherein said valve housing is movable relative to said tube to increase the distance between said flange and said plunger plate to allow said tubular elastomeric seal to expand and increase said inner diameter for establishing an open condition of the medical valve assembly;
a first pivot extending radially from said tube and a second pivot extending radially from said valve housing;
said manual actuator including a pair of lever arms pivotably connected to said first pivot and a pair of lever linkages pivotably connected to said second pivot; and
each of said lever linkages extending from said second pivot to engage one of said respective levers for allowing the user to radially compress said pair of lever arms with a force to effectuate the increase in the distance between said plunger plate and said flange.

2. The medical valve assembly as set forth in claim 1, wherein said plunger plate defines a plunger plate surface extending in spaced and parallel relationship to said axis and said valve housing overlays said plunger plate surface for allowing one of said plunger plate and said valve housing to slide relative to one another along said plunger plate surface during said axial movement.

3. The medical valve assembly as set forth in claim 1, wherein elastomeric seal includes an inner portion and an outer portion disposed axially outward from said inner portion and disposed in abutting relationship one of said plunger plate and said flange, and said inner portion having a first durometer value and said outer portion having a second durometer value being greater than said first durometer value.

4. The medical valve assembly as set in claim 1, wherein said compression member includes a coil spring radially disposed between said valve housing and said tube and compressed between said first valve housing end and said plunger plate to bias said valve housing towards said first tube end and compress said elastomeric seal between said flange and said plunger plate to establish the closed condition of the medical valve assembly.

5. The medical valve assembly as set forth in claim 4, further comprising a disk slidably disposed around said tube and interconnected to said first valve housing end to establish a shoulder extending radially inward from said valve housing and disposed in engagement with said coil spring.

6. The medical valve assembly as set forth in claim 1, wherein each of said lever arms define a track for receipt of said respective lever linkage when disposed in abutting relationship therewith.

7. The medical valve assembly as set forth in claim 1, further comprising a detachable cap disposed over said second valve housing end of said valve housing to hold said pair of lever arms in the radially compressed position and keep said elastomeric seal in the open position.

8. The medical valve assembly as set forth in claim 1, further comprising:
said tube defining a tapered portion disposed adjacent said first tube end for fitting a sheath over said tube; said tube including threads disposed adjacent said first tube end; and a nose cap threadingly secured to said first tube end for establishing a compression fit of the sheath between said cap and said tapered portion of said tube.

9. The medical valve assembly as set forth in claim 1, wherein said flange defines an opening aligned on said axis A and sized to receive the medical device.

10. The medical valve assembly as set forth in claim 9, wherein said elastomeric seal includes an inner portion comprised of a first material having a first durometer value and an outer portion comprised of a second material having a second durometer value being greater than said first durometer value, and a wiper seal extends radially from said outside portion and is disposed adjacent said opening of the valve housing.

11. A medical valve assembly, for use in inserting a medical device into a body vessel of a patient, comprising:
a tube extending between a first tube end and a second tube end to define a passageway extending along a longitudinal axis between said ends;
a plunger plate extending radially from said second tube end of said tube;
a valve housing surrounding said tube about said second tube end and extending from a first valve housing end to a second valve housing end; said valve housing including a flange extending radially inwards from said second valve housing end and disposed in spaced relationship with said plunger plate to define a distance extending therebetween;
an elastomeric seal compressed between said plunger plate and said flange and having an inner diameter for use in establishing a variable seal of the medical valve assembly;
one of said valve housing and said tube axially movable relative to the other to vary the distance between said plunger plate and said flange and adjust said inner diameter of said elastomeric seal for variably sealing the medical valve assembly to a variety of differently sized medical devices;
a coil spring radially disposed between said valve housing and said tube and compressed between said first valve housing end and said plunger plate to bias said valve housing towards said first tube end and compress said elastomeric seal between said flange and said plunger plate to establish a closed condition of the medical valve assembly;
a leaf spring cage disposed in surrounding relationship with said elastomeric seal and compressed between said plunger plate and said flange; and
said leaf spring cage including a plurality of struts each extending axially along said leaf spring cage and configured to fold radially inward towards said valve housing when said valve housing is axially biased towards said first tube end by said compression spring to decrease the distance between said plunger plate and said flange and compress said elastomeric seal for decreasing said inner diameter and further establishing the closed condition of the medical valve assembly.

12. The medical valve assembly as set forth in claim 11, further comprising a constrictor band extending around said leaf spring cage to prevent said plurality of struts from engaging said valve housing when said leaf spring cage is expanded by an insertion force of a medical device.

* * * * *